United States Patent
Peter et al.

(10) Patent No.: US 10,682,334 B2
(45) Date of Patent: Jun. 16, 2020

(54) TREATMENT FOR NON-ALCOHOLIC FATTY LIVER DISEASES

(71) Applicant: DSM IP ASSETS B.V., Heerlen (NL)

(72) Inventors: Szabolcs Peter, Kaiseraugst (CH); Joseph Schwager, Kaiseraugst (CH); Weerasinghe M. Indrasena, Kaiseraugst (CH); Jaroslav A. Kralovec, Kaiseraugst (CH); Bernd Mussler, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/166,357

(22) Filed: Oct. 22, 2018

(65) Prior Publication Data

US 2019/0054063 A1    Feb. 21, 2019

Related U.S. Application Data

(63) Continuation-in-part of application No. 15/536,252, filed as application No. PCT/EP2015/079526 on Dec. 14, 2015.

(30) Foreign Application Priority Data

Dec. 15, 2014   (CH) ...................... 1939/14

(51) Int. Cl.
| | | |
|---|---|---|
| *A61K 31/355* | (2006.01) | |
| *A61P 1/16* | (2006.01) | |
| *A61K 31/22* | (2006.01) | |

(52) U.S. Cl.
CPC .......... *A61K 31/355* (2013.01); *A61K 31/22* (2013.01); *A61P 1/16* (2018.01)

(58) Field of Classification Search
CPC .......... A61K 31/355; A61K 31/22; A61P 1/16
See application file for complete search history.

(56) References Cited

U.S. PATENT DOCUMENTS

| | | | |
|---|---|---|---|
| 4,874,603 | A | 10/1989 | Fratzer |
| 2008/0213239 | A1 | 9/2008 | Morris |
| 2019/0314328 | A1 | 10/2019 | Peter et al. |

FOREIGN PATENT DOCUMENTS

| | | |
|---|---|---|
| EP | 0 699 437 | 3/1996 |
| EP | 2 740 473 | 6/2014 |
| JP | 08175988 | 7/1996 |
| WO | 2009/028457 A1 | 12/2010 |
| WO | 2011/097273 | 8/2011 |
| WO | 2014/165190 | 10/2014 |

OTHER PUBLICATIONS

OilsandPlants (OilsandPlants, Aug. 2010) (Year: 2010).*
Velez et al. (Rev Col Gastroenterol 29, 4, 2014) (Year: 2014).*
International Search Report for PCT/EP2015/079526 dated Jan. 28, 2016, 4 pages.
Written Opinion of the ISA for PCT/EP2015/079526 dated Jan. 28, 2016, 5 pages.
Patrick L., "Nonalcoholic Fatty Liver Disease: Relationship to Insulin Sensitivity and Oxidative Stress. Treatment Approaches using Vitamin E, Magnesium, and Betaine", *Alternative Medicine Review*, vol. 7, No. 4, Jan. 1, 2002, pp. 276-291.
Final Office action for U.S. Appl. No. 15/536,252, dated Dec. 28, 2018.
Non-final Office Action for U.S. Appl. No. 15/536,252, dated Jan. 18, 2018.
Pacana, T., et al., "Vitamin E and nonalcoholic Fatty Liver Disease," Current Opinion, Vo. 15, No. 6, Nov. 2017. (w translation).
Franchinformation, Omegaven Fresenius—Emulsion zur Infusion, Omeg V5 Pv.doc/Version: 4; Austria, Apr. 2008, pp. 1-8 (no English-language Translation).

* cited by examiner

*Primary Examiner* — Umamaheswari Ramachandran
(74) *Attorney, Agent, or Firm* — Nixon & Vanderhye PC

(57) ABSTRACT

The present invention relates to the use of mixtures of vitamin E and polyunsaturated fatty acids (PUFAs) as agents for the prevention, control and/or treatment of conditions associated with excessive fat accumulation in the liver which is not caused by alcohol abuse. This includes prevention, control and/or treatment of non-alcoholic steatosis in the liver—known as non-alcoholic fatty liver disease (NAFLD)—and/or non-alcoholic steatohepatitis (NASH) in a subject in need thereof. In particular, the present invention relates to the use of such compounds comprising vitamin E acetate and DHA EE as active ingredients in the manufacture of medicaments for the prevention, control and/or treatment of conditions related to NAFLD.

10 Claims, No Drawings

TREATMENT FOR NON-ALCOHOLIC FATTY LIVER DISEASES

This application is a continuation-in-part of U.S. Ser. No. 15/536,252, filed 15 Jun. 2017, published as 2018-0000775 on 4 Jan. 2018, which is the national phase filing of PCT/EP2015/079526 filed 14 Dec. 2015, claiming priority to Swiss patent application number CH01939/14, filed 15 Dec. 2014.

The present invention relates to the use of mixtures of vitamin E and polyunsaturated fatty acids (PUFAs) as agents for the prevention, control and/or treatment of conditions associated with excessive fat accumulation in the liver which is not caused by alcohol abuse. This includes prevention, control and/or treatment of non-alcoholic steatosis in the liver—known as non-alcoholic fatty liver disease (NAFLD)—and/or non-alcoholic steatohepatitis (NASH) in a subject in need thereof. In particular, the present invention relates to the use of such compounds comprising vitamin E and PUFAs as active ingredients in the manufacture of medicaments for the prevention, control and/or treatment of conditions related to NAFLD.

Although the pathophysiology of fatty liver has not yet been fully clarified, a generally accepted mechanism is the "two-hit" theory (Day and James, 1998 Gastroenterology 114:842-845). The first hit corresponds to the accumulation of free fatty acids (FFA) in the liver, which can be related to obesity, or more generally to metabolic syndrome (including diabetes, hypertension and dyslipidemia). The second hit refers to the peroxidation of these fatty acids due to the oxidative stress produced by different factors (Angulo and Lindor, 2001 Gastroenterology 120:1281-1285).

The final result of the first hit is an excessive FFA balance, from oversupply and/or failure in lipid beta oxidation, leading to fatty acid accumulation in the liver which gives rise to the first lesions (Charlton et al., 2002 Hepatology 35:898-904). These initial impacts make the liver more vulnerable to aggressive factors of the second hit, which is mediated by oxidative stress and pro-inflammatory cytokines (TNF-α, TGF-ß, IL-6, IL-8). FFAs increase the expression of cytochrome P450 2E1 (CYP 2E1), a microsomal enzyme which takes part in the ß-oxidation of several FFAs, causing the release of reactive oxygen metabolites (Weltman et al., 1998 Hepatology 27:128-131). Also some FFAs are metabolized by peroxisomal ß-oxidation, generating additional reactive oxygen metabolites (hydrogen peroxide, hydroxyl radicals) (Rao and Reddy, 2001 Semin Liver Dis 21:43-55). An excess of these molecules depletes natural antioxidants such as glutathione and vitamin E in the liver, causing oxidative stress which results in lipid peroxidation (Neuschwander-Tetri and Caldwell, 2003 Hepatology 37:1202-1219). Consequently damage in the hepatocyte organelles and membranes occurs, leading to hepatocellular degeneration and ultimately necrosis (Garcia-Monzon et al., 2000 J Hepatol 33:716-724). Lipid peroxidation in mitochondria results in extra production of reactive oxygen metabolites, causing more oxidative stress (Solis Herruzo et al., 2006 Rev Esp Enferm Dig 98:844-874). Under these circumstances nuclear factor KB (NF-κB) will be activated, which stimulates the synthesis of inflammatory mediators such as pro-inflammatory cytokines (TNF-α, TGF-ß, IL-8) (Angulo, 2002 N Engl J Med 346:1221-1231). Besides this, final aldehyde by-products of lipid peroxidation, such as malondialdehyde (MDA), and 4-hydroxynonenal show chemotactic properties and activate pro-inflammatory cytokines (TNF-α, TGF-ß, IL-6, IL-8), and stimulate hepatic collagen-producing stellate cells (Pessayre, 2007 J Gastroenterol Hepatol 22 (Suppl 1):S20-S27). Patients with NAFLD had an increased expression of TNF-α in the liver (Crespo et al., 2001 Hepatology 34(6): 1158-1163). The final result, a mixed lesion is known as steatohepatitis, characterized by steatosis, inflammatory infiltration and fibrotic degeneration of the liver tissue, and finally hepatocyte necrosis. Ongoing oxidative stress and lipid peroxidation induce continuous collagen production which leads to fibrosis reaching the stage of hepatic cirrhosis (Chitturi and Farrell, 2001 Hepatology 36:403-409).

The liver-specific Kupffer cells seem to play an important role in the pathogenesis of fatty liver diseases such as, e.g. NASH. Kupffer cells are liver-resident macrophages providing significant protection against endotoxins and harmful exogenous particles from the portal vein. The pathogenesis of NASH may encompass hyperendotoxemia (Creely et al., 2007 Am J Physiol Endocrinol Metab. 292:E740-E747) as a consequence of impaired phagocytotic function of Kupffer cells (Loffreda et al., 1998 FASEB J. 12:57-65). Damaged clearance of bacterial metabolites, endotoxins, lipopolysaccharides etc. might speed up the pathogenesis of liver diseases. Activation of Kupffer cells leads to additional stress stimuli and may determine the fate of hepatocytes from survival toward apoptosis. In Kupffer cells overproduction of cytokines, e.g. TNF-α and IL-1B occurs. Simultaneously, Kupffer cells become more sensitive to these molecules (Diehl, 2002 Am J Physiol Gastrointest Liver Physiol. 282:G1-G5). Inflammatory mediators produced by activated Kupffer cells trigger hepatic stellate cells to synthesize collagen which might result in liver fibrosis and cirrhosis. Aggregates of hypertrophic Kupffer cells can be observed in perivenular areas of the livers of NASH patients compared with the diffuse distribution seen in case of simple steatotic liver (Park et al., 2007 J Gastroenterol Hepatol. 22:491-497).

With regards to the inflammatory events in the liver, such as associated with NAFLD or NASH, the effect of vitamin E has been examined in various human clinical studies (Pacana et al. Curr Opin Clin Nutr Metab Care 2012; 15:641-648). Through the intake of vitamin E, liver enzymes could be improved with a decrease of the plasma cytokine level. With a daily dose of 800 IU/day liver histology in non-diabetic adults with biopsy-proven NASH could be improved. However, the use of vitamin E is not recommended in diabetic patients as treatment of NASH, NAFLD without liver biopsy, NASH cirrhosis or cryptogenic cirrhosis (Chalasani et al. Hepatology, vol. 55, no. 6, 2012).

Therefore, there is a need for new agents with hepatoprotective effects but with weak or no side effects. These agents could be used for prevention, control and/or treatment of fatty liver diseases which are not caused by alcohol abuse.

In accordance with the present invention it has been found that certain compounds can modulate the biosynthesis/overproduction of inflammatory mediators which are involved in NAFLD or related malfunction of the liver, said mediators include e.g. eicosanoids (prostaglandins, leukotrienes), cytokines, chemokines, nuclear factors and/or nitric oxide.

Surprisingly, it has been found out that combinations of vitamin E and PUFAs exhibit hepatoprotective effects and are able to synergistically modulate the biosynthesis/overproduction of some pro-inflammatory mediators such as, e.g., cytokines. Therefore, such compounds are useful for the prevention, control and/or treatment of conditions associated with excessive accumulation of fat in the liver, preferably for prevention, control and/or treatment of NAFLD.

Thus, the present invention relates to the use of a mixture comprising vitamin E and PUFAs for the treatment, control and/or prevention of hepatic inflammation and cell injury in the liver, more preferably prevention, control and/or treatment of NAFLD and related diseases. Thus, in one aspect, the present invention relates to the use of vitamin E and PUFAs in the manufacture of a medicament for the prevention, control and/or treatment of conditions requiring modulation of inflammatory responses in liver cells, in particular the treatment and prevention of NAFLD.

Mixtures according to the present invention comprising vitamin E and PUFAs may be used as nutraceutical compositions, i.e. as supplement to dietary compositions, i.e., (fortified) food/feed or beverages, or as compositions in dosage unit form such as pharmaceutical compositions, e.g., tablets, granules, pastes or effervescent formulations which may further comprise pharmaceutically acceptable carriers, excipients or diluents, including, but not limited to, lubricants, colorants, wetting agents, fillers, disintegrants and flavorants. The pastes may be filled into hard or soft gelatine capsules.

As used herein, the term "vitamin E" includes both natural and synthetic mixtures of tocopherols, including α-tocopherol, ß-tocopherol, γ-tocopherol and δ-tocopherol. Tocopherol, which is liquid at room temperature, is a group of methylated phenolic compounds of the general formula (I),

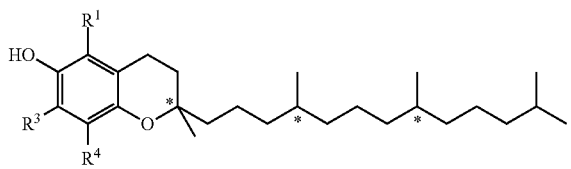

(I)

wherein R1, R3 and R4 are independently from each other hydrogen or methyl groups; and wherein each * represents an individual chiral center. With regards to the tocopherol isoforms, R1, R3 and R4 are as follows: α-tocopherol (R1=R3=R4=CH3); ß-tocopherol (R1=R4=CH3, R3=H); γ-tocopherol (R1=H, R3=R4=CH3); δ-tocopherol (R1=R3=H, R4=CH3).

It is preferred that at least one of the substituents R1 and R3 in formula (I) is CH3, more preferably is the use of α-tocopherol and/or γ-tocopherol.

The tocopherols of formula (I) have chiral carbon centers which are indicated by the asterisk (*) in the formula. The configuration at these chiral centers is defined to be either R or S, a concept which is known to the person skilled in the art.

For a given definition of residues R1, R3 and R4, the respective tocopherols according to formula (I) exist in 8 different isomers due to these chiral centers (i.e. (2R,4'R,8'R)-, (2R,4'S,8'R)-, (2R,4'R,8'S)-, (2R,4'S,8'S)-, (2S,4'R,8'R)-, (2S,4'S,8'R)-, (2R,4'R,8'S)- and (2S,4'S,8'S)-tocopherol). As used herein, the tocopherols are either present in the form of mixture of said chiral isomers or isomerically pure. The (2RS, 4'RS, 8'RS) tocopherol is also known as (all-rac)-tocopherol.

A particularly useful form of vitamin E is α-tocopherol which is used in a mixture with PUFA. Another particularly useful form is vitamin E acetate which is used in a mixture with PUFA.

PUFAs are classified according to the position of the double bonds in the carbon chain of the molecule as n-9, n-6 or n-3 PUFAs. Examples of n-6 PUFAs are linoleic acid (C18:2), arachidonic acid (C20:4), γ-linolenic acid (GLA, C18:13) and dihomo-γ-linolenic acid (DGLA, C20:3). Examples of n-3 PUFAs are α-linolenic acid (C18:13), eicosapentaenoic acid (EPA, C20:5), and docosahexaenoic acid (DHA, C22:6). Especially EPA and DHA have attracted interest of the food industry in recent years. The most available sources of these two fatty acids are fish and the marine oils extracted from them or microalgae.

As used herein, the term "PUFAs" or "PUFA" refers to a fatty acid having a backbone comprising 16 or more carbon atoms, (for example, 16, 18, 20 or 22 carbon atoms (C16, C18, C20, or C22, respectively), and two or more carbon-carbon double bonds in the backbone. As used herein, a "long-chain PUFA" (LC-PUFA) refers to a fatty acid having a backbone comprising 18 or more carbon atoms, and two or more carbon-carbon double bonds in the backbone, for example, C18:3n-3 (alpha-linolenic acid or ALA). When the notation CA:Bn-X is used for a methylene-interrupted PUFA, the "CA" is the number of carbons (for example C18, C20 or C22), B is the number of double bonds and X is the position of the first double bond counted from the methyl end of the fatty acid chain.

As used herein, PUFAs encompass the free acid forms thereof, as well as salts and esters thereof. As used herein, the term ester refers to the replacement of the hydrogen in the carboxylic acid group of a PUFA molecule with another substituent. Examples of common esters include methyl, ethyl, trichloroethyl, propyl, butyl, pentyl, tert butyl, benzyl, nitrobenzyl, methoxybenzyl and benzhydryl. Other esters of PUFAs are described in US 2010-0130608 A1, which is incorporated herein by reference.

PUFAs for use with the present invention include omega-3, omega-6, and omega 9 polyunsaturated fatty acids, and oxylipins derived therefrom. Exemplary omega-3 PUFAs for use with the present invention include, but are not limited to, α-linolenic acid (C18:3n-3), C18:4n-4, ω-3 eicosapentaenoic acid (20:5n-3) (eicosapentaenoic acid), ω-3 docosapentaenoic acid (docosapentaenoic acid), ω-3 docosahexaenoic acid (22:6n-3), docosatetraenoic acid (22:4n-6), and combinations thereof. Exemplary omega-6 PUFAs for use with the present invention include, but are not limited to, γ linolenic acid, linoleic acid, conjugated linoleic acid, arachidonic acid (20:4n-6), ω-6 docosapentaenoic acid, and combinations thereof. In some embodiments, a PUFA oil for use with the present invention is all-cis.

In some embodiments, the PUFA comprises DHA, also known by its chemical name (all-Z)-4,7,10,13,16,19-docosahexaenoic acid, as well as any salts or derivatives thereof. Thus, the term DHA encompasses DHA ethyl ester (DHA-EE) as well as DHA free fatty acids, phospholipids, other esters, monoglycerides, diglycerides, and triglycerides containing DHA. DHA is an ω-3 PUFA.

In a preferred form, the DHA is DHA ethyl ester.

In a preferred mixture, the Vitamin E is Vitamin E acetate ("Vit E Acetate") and the DHA is DHA ethyl ester ("DHA EE"). The DHA ethyl ester chosen is preferably a high concentration form, preferably at least 92% by weight, more preferably at least 94% by weight (prior to mixing with the Vit E acetate). In some embodiments it is at least 95% by weight prior to mixing with Vit E Acetate. These high concentration forms of DHA EE can be obtained commercially from DSM Nutritional Products, Switzerland. In this preferred mixture, the Vit E acetate is present in the mixture in an amount from 500 IU to 2000 IU per daily dose. In a preferred embodiment, the amount of Vit E Acetate present will range from 8000 IU to 1200 IU per daily dose. In some particularly preferred embodiments, the Vit E actetate is 1000 IU per daily dose.

The amount of DHA EE which is mixed with Vit E Ac can range from 500 mg to 3 grams per daily dose. In a preferred embodiment, the DHA EE will range from 1.5 grams to 2.5 grams per daily dose. In some particularly preferred embodiments, the amount of DHA EE is 2 grams. The daily dose may be split into multiple capsules (or other delivery form) for the ease of administration to the patient.

Thus, some particularly preferred compositions of the invention comprise:
1000 IU Vit E Ac and 2 grams DHA EE at per daily dose;
800-1200 IU Vit E Ac and 1.5-2.5 g DHA EE per daily dose;
800 IU Vit E Ac and 1.5 g DHA EE per daily dose; and
1200 IU Vit E and 2.5 g DHA EE per daily dose.

In further embodiments, the PUFA comprises EPA, known by its chemical name (all-Z)-5,8,11,14,17-eicosapentaenoic acid, as well as any salts or derivatives thereof. Thus, the term EPA encompasses the free acid EPA as well as EPA alkyl esters and triglycerides containing EPA. EPA is an ω-3 PUFA.

In some embodiments, the PUFA oil that is used to make the thermally stable emulsion, is substantially free of one or more specific fatty acids. For example, a PUFA oil that contains DHA-EE can be substantially free of EPA. On the other hand, a PUFA oil that contains EPA-EE can be substantially free of DHA.

Commercially available PUFAs suitable for use with the present invention include, but are not limited to, Martek DHA™ S Oil (Martek Biosciences Corp., Columbia, Md.), Rosemary-Free Martek DHA™ S Oil (Martek Biosciences Corp., Columbia, Md.), Microalgae DHA™ Oil (Martek Biosciences Corp., Columbia, Md.), OMEGAPURE® oils (Omega Protein Corp., Houston, Tex.), MARINOL® Oils (Lipid Nutrition, Wormerveer, NL), MEG-3 oils and powders (Ocean Nutrition Corp., Dartmouth, Calif.), Evogel (Symrise AG, Holzminden, Del.), Marine Oil (Arista Industries, Wilton, Conn.), and OMEGASOURCE® oils (Source Food Technology, Inc., Raleigh, N.C.).

A particularly useful form of PUFA is ω-3 PUFA which is used in a mixture with vitamin E, in particular α-tocopherol in accordance with the present invention, i.e. for the treatment, control and/or prevention of conditions associated with excessive fat accumulation in the liver which is not caused by alcohol abuse.

PUFA's are preferably used in a concentration so that the daily consumption by a human adult (weighing about 70 kg) is in the range of from 10 mg/day to 4000 mg/day, preferably from 200 mg/day to 600 mg/day, more preferably about 400 mg/day. A food or beverage suitably contains about 5 mg to about 1000 mg of a PUFA per serving. If the nutraceutical composition is a pharmaceutical formulation such formulation may contain a PUFA in an amount from about 10 mg to about 1000 mg per dosage unit, e.g., per capsule or tablet, or from about 10 mg per daily dose to about 4000 mg per daily dose of a liquid formulation.

Vitamin E or its derivative is preferably used in a concentration so that the daily consumption by a human adult (weighing about 70 kg) is in the range of from 5 mg/day to 2000 mg/day, preferably 15 to 50 IU/day, more preferably 30 IU/day. A food or beverage suitably contains about 2 mg to about 500 mg of vitamin E per serving. If the nutraceutical composition is a pharmaceutical formulation such formulation may contain vitamin E in an amount from about 5 mg to about 1000 mg per dosage unit, e.g., per capsule or tablet, or from about 5 mg per daily dose to about 2000 mg per daily dose of a liquid formulation.

The term "subject" as used herein includes, all higher animals wherein inflammatory events are known. In particular, a subject is a mammal, including animals or humans.

As used herein, a "fatty liver" or "excessive fat accumulation" associated with NAFDL or NASH means that the liver contains more than about 5 to about 10 wt % of fat.

As stated above, the compounds according to the present invention have hepatoprotective properties and are useful for the prevention, control and/or treatment of conditions involved in NAFLD or related malfunction of the liver. They can also be used as an adjunct to the treatment of a variety of diseases or disorders caused by excessive non-alcoholic fat accumulation in the liver via modulation of biosynthesis/overproduction of inflammatory mediators in the liver cells.

In a particular embodiment, the compounds of the present invention are used for the prevention, control and/or treatment of conditions associated with excessive fat accumulation in the liver which is not caused by alcohol abuse, preferably prevention, control and/or treatment of NAFLD and NASH.

Thus, the present invention is particularly directed to the use of a combination of vitamin E and PUFAs as defined above (in the manufacture of a medicament/composition) for the prevention, control and/or treatment of conditions requiring modulation of inflammatory response associated with accumulation of fat in the liver which is not caused by consumption/abuse of alcohol, especially of those conditions mentioned above.

In a further embodiment, compounds/mixtures of the present invention may be used in combination with other nutraceutical compositions or therapeutic agents known to those skilled in the art for treatment, control and/or prevention of inflammatory disorders in the liver by administration prior to, simultaneously with or following the administration of the compound(s) as disclosed herein.

Depending on the mode of administration, compounds/mixtures according to the present invention consist substantially of vitamin E and PUFA—i.e. being the main active ingredients—with furthermore addition of binders, fillers, carriers, excipients including water, glycerol, etc. known to the skilled person.

According to the present invention, the ratio of vitamin E and polyunsaturated fatty acids which is administered might be in the range of about 1:1 to about 1:5, such as e.g., 1:2, or in the range of about 4:1 or about 5:1 to about 20:1, calculated as weight ratio. Particularly, the vitamin E is calculated as α-tocopherol. Useful ratios might be in an embodiment, the polyunsaturated fatty acid and vitamin E calculated as a weight ratio of 0.2:1, 0.4:1, 0.6:1, 1:1, 2:1, 3:1, 4:1, 5:1, 6:1, 8:1, 10:1, 12:1, 14:1, 16:1, 18:1, 20:1, 25:1 or 30:1, wherein the vitamin E is calculated as α-tocopherol.

In order to determine anti-inflammatory properties of compounds or combinations thereof, appropriate cells or cell lines (i.e. whole blood, macrophages, leukocytes) will be activated with inflammatory stimuli in vitro in the presence of the compounds. This leads to the secretion of pro-inflammatory prostaglandin $E_2$ (i.e. the product of cyclooxygenase-2), nitric oxide (synthesized by inducible nitric oxide synthase) and various cytokines and interleukins. Due to their anti-inflammatory effects, compounds will reduce the level of the two metabolites. Similarly, the expression of genes of inflammatory pathways will be monitored by quantitative PCR or by micro-array analysis. Anti-inflammatory compounds reduce their expression levels. Additive and/or synergistic effects of compounds will be identified both at the level of specific inflammatory parameters and more generally in the gene expression profile related to the cellular inflammatory response.

The anti-inflammatory effect of a combined therapy with vitamin E and PUFAs can be demonstrated in stimulated macrophages including Kupffer cells by determining the inhibition of the synthesis of cytokines that reflect the inflammatory response.

In order to induce an in vitro 'inflammatory response' related to NAFLD, Kupffer cells, i.e. liver-resident macrophages, are an ideal cell type to study the hepatoprotective effects of a test substance, such as mixtures of vitamin E and PUFA according to the present invention. Alternatively, murine macrophages RAW264.7 or even monocyte/macrophages present in peripheral blood cells can be used appropriate surrogate models (Raptis et al. J Hepatology 60, 625-632, 2014). For in vitro experiments, cells may be seeded into microtiter plates or 12-well plates and stimulated with lipopolysaccharide (LPS) without or with graded amounts of the test substances. Vehicle concentrations (i.e. DMSO) are kept constant. Culture supernatants may be harvested after appropriate periods of time (e.g. 24 hours). Cytokines and interleukins can be measured by appropriate ELISA-based multiplex assays. The percentage of inhibition of the mentioned inflammatory mediators present in the liver-specific cells at a given concentration of the test substances (compared to maximal production by LPS-stimulated cells) is calculated and the putative synergistic effect of the test substance computed (see below).

The following examples are illustrative only and are not intended to limit the scope of the invention in any way. The contents of all references, patent applications, patents and published patent applications, cited throughout this application are hereby incorporated by reference.

EXAMPLES

Example 1: Synergistic Effect of Vitamin E and PUFA in Leucocytes

Experimental Procedures:

Leukocytes are obtained from healthy donors. Mononuclear cells (MNC) are purified by Ficoll-Isopaque gradient centrifugation. Cells (at 3-8×106 cells/mL) are cultured in phenol-red free RPMI 1640, supplemented with 0.25% FBS, 0.1 mM NEAA, 50 U/mL penicillin, 50 µg/mL streptomycin and 5×10-5 M 2-mercaptoethanol. Cells are stimulated with LPS (100 ng/mL) and IFN-γ (20 U/mL) for 2-24 h. Multiparametric kits for determination of cytokines and chemokines are purchased from BIO-RAD Laboratories (Hercules, Calif.) and used in the LiquiChip Workstation IS 200 (Qiagen, Hilden, Germany). The data are evaluated with the LiquiChip Analyser software (Qiagen).

The algorithm developed by Chou and Talalay is used to calculate synergistic effects (Chou, T-C. Et Talalay, P. A simple Biol. Chem. 252, 6438-6442, 1977; Chou, T-C. Et Talalay, P. Analysis of combined drug effects—A new look at a very old problem. Trends in Biological Sciences. November 1983, p 450-454, 1983). Interactions are quantified by the Combination Index (CI). Briefly, the % of inhibition of the concentration of each single substance alone or the mixture of both are determined. The affected fraction (fa) (values between 0 and 1) and unaffected fraction (fu) (1-fa), respectively, is calculated. For median-effect plots, log (fa/fu) is plotted against log (D), where D represents the concentration of each single compound alone or the mixture of both. Using CalcuSyn software (Biosoft, Ferguson, Mo.), which is based upon the method by Chou & Talalay, a CI is computed for every fraction affected: a CI<1 reflects synergistic inhibition of the respective inflammatory parameter; if CI=1 the substances have additive interactions; when CI>1 the interaction of substances reflects antagonism. It has also been observed that substances can have synergistic or antagonistic interactions at given concentrations or ratios, respectively (see e.g. Pappa et al. Quantitative combination effects between sulforaphane and 3,3'-generalized equation for the analysis of multiple inhibitions in Michaelis-Menten kinetic systems. J. diindolylmethane on proliferation of human colon cancer cells in vitro. Carcinogenesis 28, 1471-77, 2007).

Results:

Cells are stimulated with LPS, an pathogen-derived component that induces inflammatory response, which is reflected in the expression of inflammatory genes and the secretion of cytokines, interleukins and chemokines (Table 1). LPS induces a massive increase of the secretion of inflammatory mediators such as TNF-alpha. Concomitantly, inflammatory mediators are secreted. These parameters are modulated by pre-incubating cells with α-tocopherol or ω-3 PUFA prior to the stimulation with LPS. For instance, the pro-inflammatory cytokine TNF-γ is reduced by 29% and 64%, respectively (Table 1a). IL-1beta and CCL4/MIP-1b are also significantly reduced by the two substances (Tables 1b, 1c). Thus, the substances reduces the extent of the inflammatory stress in cells that respond to inflammatory stimuli.

When α-tocopherol and ω-3 PUFA s are combined at different concentrations and ratios, significant synergistic effects are observed in the inhibition of the production of the pro-inflammatory cytokine TNF-alpha, but also of the pro-inflammatory interleukin IL-1beta, as well as the chemokine CCL4 (see Tables 1a-c, right column). The synergistic effects are most prominent for TNF-alpha.

TABLE 1

Synergistic effects of α-tocopherol and ω-3 PUFA in the inflammatory response of leukocytes.

1a: synergism between AT and ω-3 PUFA in inhibiting TNF-alpha

| Treatment | pg/mL ± SD TNF-alpha | % inhibition (vs LPS) | p (vs LPS) | Combined index |
|---|---|---|---|---|
| LPS | 5290 ± 240 | — | — | — |
| AT 10 µM + LPS | 5505 ± 177 | −4 | 0.415 | |
| AT 50 µM + LPS | 3755 ± 21 | 29 | 0.012 | |
| AT 200 µM + LPS − α | 3870 ± 14 | 27 | 0.014 | — |
| DHA 10 µM + LPS | 3190 ± 14 | 60 | 0.007 | — |
| DHA 20 µM + LPS | 3400 ± 523 | 64 | 0.043 | — |
| DHA 50 µM + LPS | 3105 ± 163 | 59 | 0.009 | — |
| (AT 10 + DHA 10) + LPS | 1810 ± 269 | 34 | 0.005 | 0.04 |
| (AT 10 + DHA 20) + LPS | 2845 ± 516 | 54 | 0.026 | 0.06 |
| (AT 10 + DHA 50) + LPS | 3025 ± 417 | 57 | 0.022 | 0.16 |
| (AT 50 + DHA 10) + LPS | 1800 ± 14 | 34 | 0.002 | 0.18 |
| (AT 200 + DHA 10) + LPS | 1705 ± 431 | 32 | 0.009 | 0.70 |

1b: synergism between AT and ω-3 PUFA in inhibiting CCL4/MIP-1beta

| Treatment | pg/mL ± SD CCL4 | % inhibition (vs LPS) | p (vs LPS) | Combined index |
|---|---|---|---|---|
| LPS | 99000 ± 11341 | — | — | — |
| AT 10 µM + LPS | 91400 ± 5657 | 7 | 0.485 | |
| AT 50 µM + LPS | 83900 ± 3111 | 15 | 0.210 | |
| AT 200 µM + LPS − α | 87950 ± 3165 | 11 | 0.315 | — |

TABLE 1-continued

Synergistic effects of α-tocopherol and ω-3 PUFA in the inflammatory response of leukocytes.

| | | | | |
|---|---|---|---|---|
| DHA 10 μM + LPS | 79995 ± 3465 | 32 | 0.151 | — |
| DHA 20 μM + LPS | 67000 ± 7523 | 62 | 0.079 | — |
| DHA 50 μM + LPS | 37600 ± 778 | 62 | 0.024 | — |
| (AT 10 + DHA 10) + LPS | 61700 ± 6930 | 38 | 0.058 | 0.44 |
| (AT 50 + DHA 10) + LPS | 67800 ± 283 | 32 | 0.062 | 0.56 |
| (AT 200 + DHA 10) + LPS | 75359 ± 495 | 24 | 0.098 | 0.77 |

1c: synergism between AT and ω-3 PUFA in inhibiting IL-1beta

| Treatment | pg/mL ± SD IL-1beta | % inhibition (vs LPS) | p (vs LPS) | Combined index |
|---|---|---|---|---|
| LPS | 6310 ± 170 | — | — | — |
| AT 10 μM + LPS | 6770 ± 438 | −7 | 0.301 | |
| AT 50 μM + LPS | 5735 ± 134 | 9 | 0.064 | |
| AT 200 μM + LPS − α | 5430 ± 113 | 14 | 0.026 | — |
| DHA 10 μM + LPS | 5405 ± 742 | 14 | 0.235 | — |
| DHA 20 μM + LPS | 4865 ± 1633 | 23 | 0.339 | — |
| DHA 50 μM + LPS | 1440 ± 71 | 77 | 0.001 | — |
| (AT 10 + DHA 10) + LPS | 3520 ± 71 | 44 | 0.002 | 0.41 |
| (AT 10 + DHA 20) + LPS | 3645 ± 884 | 42 | 0.053 | 0.83 |
| (AT 10 + DHA 50) + LPS | 796 ± 41 | 87 | 0.001 | 0.63 |
| (AT 50 + DHA 10) + LPS | 3570 ± 113 | 43 | 0.003 | 0.54 |
| (AT 50 + DHA 50) + LPS | 1013 ± 95 | 83 | 0.001 | 0.77 |
| (AT 200 + DHA 10) + LPS | 3455 ± 106 | 45 | 0.002 | 0.95 |
| (AT 200 + DHA 50) + LPS | 1080 ± 28 | 83 | 0.001 | 0.95 |

AT = α-tocopherol; for more details see text.

Example 2: Soft Gelatin Capsule

Soft gelatin capsules are prepared by conventional procedures providing a dose of vitamin E of 5 to 1000 mg (e.g. α-tocopherol), such as e.g. 50 mg, and at least one compound selected from the group of PUFAs as defined above of 10 to 1000 mg (e.g. DHA), such as e.g. 200 mg, wherein the amounts are the recommended daily doses. Other ingredients to be added: glycerol. Water, gelatine, vegetable oil.

Example 3: Hard Gelatin Capsule

Hard gelatin capsules are prepared by conventional procedures providing a dose of vitamin E of 5 to 1000 mg (e.g. α-tocopherol) and at least one compound selected from the group of PUFAs as defined above of 10 to 1000 mg (e.g. DHA), wherein the amounts are the recommended daily doses. Other ingredients to be added: fillers, such as, e.g., lactose or cellulose or cellulose derivatives q.s.; lubricant, such as, e.g., magnesium stearate if necessary (0.5%).

Example 4: Tablet

Tablets are prepared by conventional procedures providing as active ingredient 5 to 1000 mg of vitamin E (e.g. α-tocopherol), such as e.g. 20 mg, per tablet and at least one compound selected from the group of PUFAs as defined above of 10 to 1000 mg (e.g. DHA), and as excipients microcrystalline cellulose, silicone dioxide ($SiO_2$), magnesium stearate, crospovidone NF (which is a disintegratent agent) ad 500 mg.

Example 5: Soft Drink

An orange juice drink colored with beta-Carotene 10% CWS and with vitamin E (e.g. α-tocopherol) and at least one compound selected from the group of PUFAs as defined above (e.g. DHA) may be prepared according to Table 2 and 3.

TABLE 2

| Soft drink ingredients | |
|---|---|
| Sugar syrup 64°Brix | 156.2 g |
| Sodium benzoate | 0.2 g |
| Ascorbic acid, fine powder | 0.2 g |
| Citric acid 50% w/w | 5.0 g |
| Pectin solution 2% w/w | 10.0 g |
| Vitamin E | 2-500 mg |
| PUFA | 5-1000 mg |
| Juice compound (see Table 3) | 30.0 g |
| Water to | 250.0 g |

First, sodium benzoate is dissolved in water whilst stirring. Stirring is continued and sugar syrup, ascorbic acid, citric acid, pectin solution and juice compound are added one after the other. Do not use a high speed mixer. The bottling syrup is diluted with (carbonated) water to one liter of beverage.

TABLE 3

| Ingredients Juice compound | |
|---|---|
| Orange juice concentrate 65°Brix | 483.3 g |
| Lemon juice concentrate 45°Brix | 173.3 g |
| Oily orange flavor | 5.0 g |
| Beta-carotene 10% CWS as 10% stock solution | 10.0 g |
| Deionized water | 328.4 g |

For preparation of the juice compound, deionized water is first added to the juice concentrates with gently stirring to allow the juice concentrates to hydrate. Then, the oily flavor and beta-carotene 10% CWS stock solution are added and pre-emulsified in a rotor-stator-homogenizer. Homogenization is performed in a high-pressure homogenizer at 200 bar.

Typical serving of a soft drink can be 240 ml, with an amount in Vitamin E (e.g. α-tocopherol) which is about 5-100 mg/serving and an amount in PUFA (e.g. DHA) which is about 5-500 mg/serving

Example 6: Synergistic Effect of Vitamin E and PUFA in Kupffer Cells

The present study is extended to macrophages isolated from murine or human liver: Adherent cells (i.e. Kupffer cells) are obtained from liver tissue. Isolation and cultivation is done according to the method described by Li et al., Immonological Letters 158, 52-56, 2014 or according to any method known in the art. These cells are treated with compounds as described above (see Example 1). These cells will be activated with an inflammatory stimulus and the effect of substances and combination thereof on the reduction of the inflammatory response is determined. With this set-up, identical effects as those described for blood cell derived macrophages (see Ex. 1) are obtained.

The invention claimed is:

1. A method of treating a condition requiring modulation of inflammatory response associated with accumulation of fat in the liver which is not caused by consumption/abuse of alcohol, comprising administering to a subject in need thereof, vitamin E acetate ("Vit E acetate") and docosahexaenoic acid ethyl ester ("DHA EE") wherein the ratio of Vit E acetate to DHA EE provides a synergistic effect and is in the range of about 1:1, 1:2, 1:5 or in the range of about 5:1 or 20:1, wherein the vitamin E acetate is calculated as α-tocopherol and the ratio is calculated as weight ratio, wherein the amount of Vit E acetate administered is from 500-2000 IU per day and the amount of DHA EE administered is from 500 mg to 3 grams per day, and wherein the inflammatory response is non-alcoholic fatty liver disease (NALFD) or non-alcoholic steatohepatitis (NASH).

2. The method according to claim 1, wherein the amount of Vit E acetate administered is 1000 IU per day.

3. The method according to claim 1, wherein the amount of Vit E acetate administered is from 800-1200 IU.

4. The method according to claim 1, wherein the amount of DHA EE administered is from 1.5 grams to 2.5 grams per day.

5. The method according to claim 1, wherein the amount of DHA EE administered is 2 grams per day.

6. The method according to claim 1, which comprises daily administering of the Vit E acetate and DHA EE by multiple doses.

7. A method of treating a condition requiring modulation of inflammatory response associated with accumulation of fat in the liver which is not caused by consumption/abuse of alcohol, comprising administering to a subject in need thereof, Vit E acetate and DHA EE, wherein the daily dose is selected from the group consisting of:
 a) 1000 IU Vit E Ac and 2 grams DHA EE at per daily dose;
 b) 800-1200 IU Vit E Ac and 1.5-2.5 g DHA EE per daily dose;
 c) 800 IU Vit E Ac and 1.5 g DHA EE per daily dose; and
 d) 1200 IU Vit E and 2.5 g DHA EE per daily dose,
 wherein the Vit E acetate and DHA EE provides a synergistic effect, and wherein the inflammatory response is non-alcoholic fatty liver disease (NALFD) or non-alcoholic steatohepatitis (NASH).

8. A method of modulating the biosynthesis or overproduction of inflammatory mediators associated with accumulation of fat in the liver which is not caused by consumption/abuse of alcohol, comprising administering to a subject in need thereof, Vit E acetate and DHA EE, wherein the ratio of Vit E acetate to DHA EE is in the range of about 1:1, 1:2, 1:5 or in the range of about 5:1 or 20:1, wherein the vitamin E acetate is calculated as α-tocopherol and the ratio is calculated as weight ratio, wherein the ratio of Vit E acetate to DHA EE provides a synergistic effect, and wherein the biosynthesis or overproduction of inflammatory mediators is associated with non-alcoholic fatty liver disease (NALFD) or non-alcoholic steatohepatitis (NASH).

9. A method of modulating inflammatory responses in liver cells associated with accumulation of fat in the liver which is not caused by consumption/abuse of alcohol, comprising administering to a subject in need thereof, Vit E acetate and DHA EE, wherein the ratio of Vit E acetate to DHA EE is in the range of about 1:1, 1:2, 1:5 or in the range of about 5:1 or 20:1, wherein the vitamin E acetate is calculated as α-tocopherol and the ratio is calculated as weight ratio, wherein the ratio of Vit E acetate to DHA EE provides a synergistic effect, and wherein the inflammatory response is associated with non-alcoholic fatty liver disease (NALFD) or non-alcoholic steatohepatitis (NASH).

10. A method of reducing the expression levels of inflammatory mediators associated with accumulation of fat in the liver which is not caused by consumption/abuse of alcohol, comprising administering to a subject in need thereof, Vit E acetate and DHA EE, wherein the ratio of Vit E acetate to DHA EE is in the range of about 1:1, 1:2, 1:5 or in the range of about 5:1 or 20:1, wherein the vitamin E acetate is calculated as α-tocopherol and the ratio is calculated as weight ratio, wherein the ratio of Vit E acetate to DHA EE provides a synergistic effect, and wherein the expression level of inflammatory mediators is associated with non-alcoholic fatty liver disease (NALFD) or non-alcoholic steatohepatitis (NASH).

\* \* \* \* \*